United States Patent [19]

Fischer et al.

[11] Patent Number: 5,030,328
[45] Date of Patent: Jul. 9, 1991

[54] METHOD OF SEPARATING γ-BUTYROLACTONE FROM MIXTURES CONTAINING DIETHYL SUCCINATE

[75] Inventors: Rolf Fischer, Heidelberg; Peter Stops, Altrip; Erwin Brunner, Ludwigshafen; Rudolf Weigand, Bruehl, all of Fed. Rep. of Germany

[73] Assignee: BASF Aktiengesellschaft, Ludwigshafen, Fed. Rep. of Germany

[21] Appl. No.: 609,435

[22] Filed: Nov. 5, 1990

[30] Foreign Application Priority Data

Nov. 16, 1989 [DE] Fed. Rep. of Germany ....... 3938121

[51] Int. Cl.$^5$ .................. B01D 3/14; C07D 301/32; C07D 307/33
[52] U.S. Cl. ....................................... 203/80; 203/78; 203/DIG. 19; 549/295; 568/864
[58] Field of Search ............ 203/73, 78, 80, 84, 203/71, DIG. 19, 99, 14, 91, 77; 549/295, 429, 509; 568/864, 868, 869; 560/191, 190

[56] References Cited

U.S. PATENT DOCUMENTS

| 4,767,869 | 8/1988 | Harrison et al. | 549/295 |
| 4,919,765 | 4/1990 | Wilkes et al. | 203/77 |
| 4,945,173 | 7/1990 | Wood | 568/864 |

FOREIGN PATENT DOCUMENTS

| 59-27881 | 2/1984 | Japan | 549/295 |
| 62-111976 | 5/1987 | Japan | 549/295 |
| 787927 | 12/1957 | United Kingdom | 549/295 |
| 2175894 | 12/1986 | United Kingdom | 549/295 |

Primary Examiner—Wilbur Basscomb
Attorney, Agent, or Firm—John H. Shurtleff

[57] ABSTRACT

A method of separating γ-butyrolactone from a mixture containing ethanol, tetrahydrofuran, water, n-butanol, 1,4-butanediol, diethyl succinate and γ-butyrolactone, by distillation in vacuum columns.

1 Claim, 1 Drawing Sheet

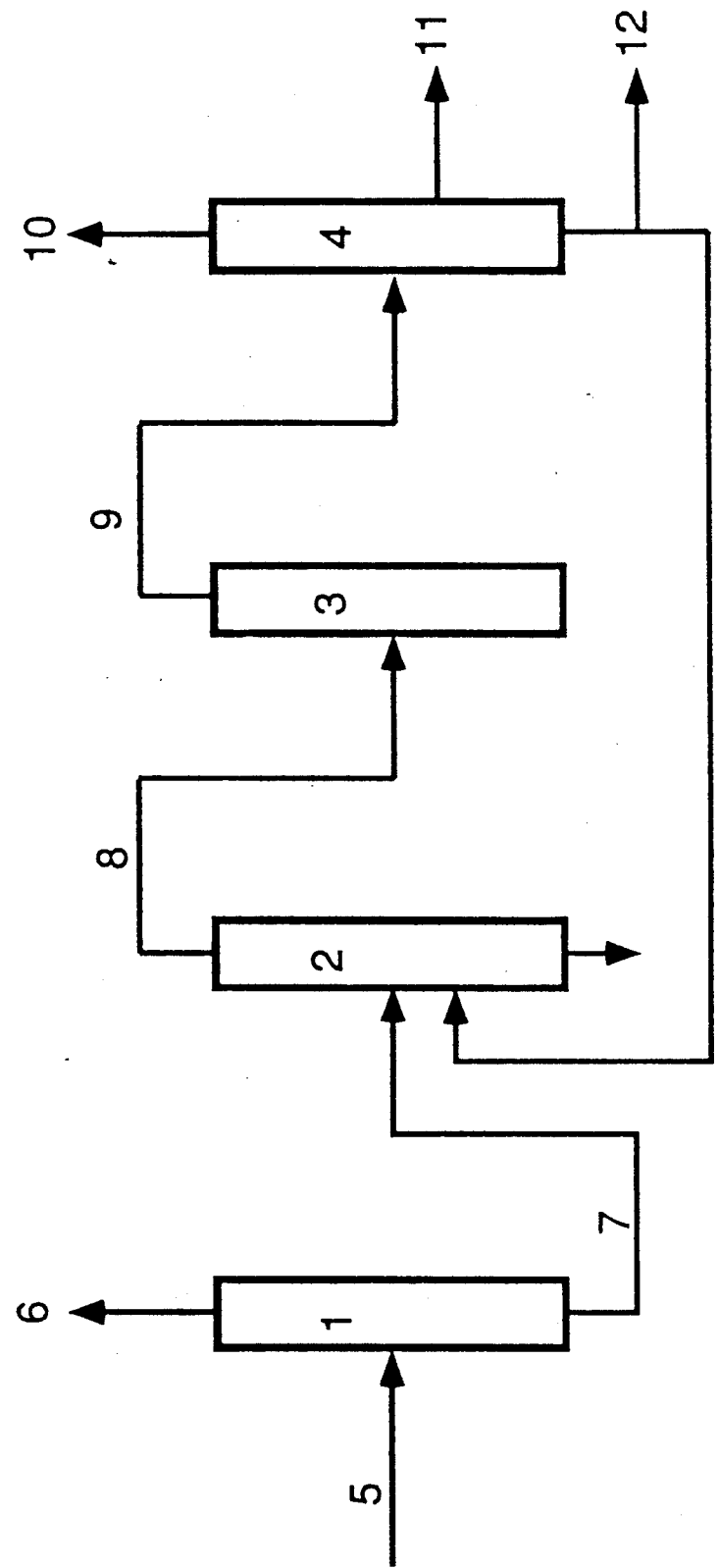

METHOD OF SEPARATING γ-BUTYROLACTONE FROM MIXTURES CONTAINING DIETHYL SUCCINATE

The present invention relates to a method of separating γ-butyrolactone from a mixture containing ethanol, tetrahydrofuran, water, n-butanol, 1,4-butanediol, diethyl succinate and γ-butyrolactone, by distillation.

1,4-Butanediol, an important intermediate in the synthesis of polyesters, is prepared, for example, by hydrogenation of the diethyl ester of maleic, fumaric or succinic acid. This process produces a mixture which contains, besides 1,4-butanediol (BD), γ-butyrolactone (GBL), tetrahydrofuran (THF), diethyl succinate (DES), ethanol, n-butanol, water and minor quantities of high-boiling by-products.

When such a mixture is worked up, it is desirable to obtain not only the main product BD but also the other useful products THF and GBL in a pure form.

The isolation of pure GBL from said mixtures is not possible by normal distillation, since GBL forms an azeotrope with DES. EP-A 256,813 proposes, therefore, that the DES be separated from such mixtures containing GBL by extraction with an organic solvent. According to a preferred embodiment, the extract consisting of DES and organic solvent is subsequently extracted with a polar solvent such as water. This separating process is costly, since two additional substances are required and the subsequent separation of the water by distillation involves high energy costs.

EP-A 255,400 describes a method of producing pure GBL whereby the problem of the azeotrope formed by GBL and DES is avoided by adding diethyl maleate. The mixture of BD, THF, GBL, DES, ethanol, n-butanol and water produced by catalytic hydrogenation of diethyl maleate, fumarate or succinate is distilled in a first column such that ethanol, water, THF and n-butanol are removed at the top, whilst all other components remain at the bottom of the column. The bottoms from the first column are then distilled in a second column such that the GBL/DES azeotrope is removed at the top and the BD remains at the bottom. Purification of the GBL is effected by passing the overheads from the second column to a third column together with a suitable amount of diethyl maleate as used as starting material for the catalytic hydrogenation. Pure GBL is removed at the top of the column.

The bottoms, consisting of diethyl maleate and DES, can be recycled to the hydrogenation stage.

The overheads from the first column must be separated by passage through a number of further columns so as to recover on-specification THF, and to make it possible to recycle ethanol suitable for the esterification of monobutyl maleate and to remove water and n-butanol. Furthermore, the bottoms from the second column must be distilled to give on-specification BD. Thus this process involves high separating costs and demands a large number of distilling columns.

We have now found that GBL can be isolated, by distillation, from a mixture containing ethanol, THF, water, n-butanol, BD, DES and GBL in a far more advantageous manner by (a) separating the THF, water and up to 99% of the ethanol as overheads in a first column having from 5 to 25 theoretical trays and operated at a pressure of from 50 to 500 mbar and a temperature of from 35° to 50° C., both as measured at the top of the column, (b) feeding the bottoms from the first column to a second column having from 10 to 30 theoretical trays and operated under a pressure of from 20 to 200 mbar and a temperature of from 45° to 60° C., both as measured at the top of the column, to give overheads consisting of ethanol, n-butanol, GBL, DES and BD, (c) feeding the overheads from the second column to a third column having from 40 to 100 theoretical trays and operated under a pressure of from 20 to 200 mbar and a temperature of from 50° to 65° C., both as measured at the top of the column, to give overheads consisting of ethanol, n-butanol and GBL and (d) feeding the overheads from the third column to a fourth column having from 10 to 30 theoretical trays and operated under a pressure of from 50 to 500 mbar and a temperature of from 45° to 55° C., both as measured at the top of the column, to give overheads consisting of ethanol and n-butanol, whilst the GBL is removed from the column through a side outlet.

The GBL-containing mixtures used for treatment by our novel process come, for example, from the well known catalytic hydrogenation of ethyl esters of maleic, fumaric and/or succinic acids. Their composition may be as follows, for example: from 40 to 55% w/w of ethanol, from 0.5 to 10% w/w of THF, from 0.05 to 2% w/w of n-butanol, from 0.005 to 4% w/w of water, from 2 to 10% w/w of GBL, from 20 to 50% w/w of BD, from 2 to 10% w/w of DES and from 0.1 to 1% w/w of high-boiling fractions.

The novel process involves the use of four vacuum columns and is carried out, for example, as described below.

In the first column, which has from 5 to 25 theoretical trays, the THF, water and up to 99%, preferably from 97 to 99% w/w of the ethanol present in the mixture are distilled off from the latter and removed as overheads. The temperature and pressure at the top of the column are, for example, 35°–50° C. and 50–500 mbar respectively. The reflux ratio is, for example, 0.2 to 1. The bottoms from the first column, which contain n-butanol, GBL, BD, DES, the remainder of the ethanol and high-boiling fractions, are fed to the second column having from 10 to 30 theoretical trays, in which the ethanol, n-butanol, GBL, DES and part of the BD, which forms an azeotrope with the DES, are removed at the top, where the temperature and pressure are from 45° to 60° C. and from 20 to 200 mbar respectively. The reflux ratio is from 1 to 10. The bottoms in the second column contain the major portion of the BD and the high-boiling fractions.

The overheads from the second column consisting, for example, of from 40 to 90% and in particular from 55 to 60% molar of GBL, from 10 to 40% and in particular from 25 to 31% molar of DES, from 0.1 to 10% and in particular from 1 to 4% molar of BD, from 1 to 20% and in particular from 5 to 10% molar of ethanol and from 0.1 to 10% and in particular from 1 to 3% molar of n-butanol are passed to the third column having from 40 to 100 theoretical trays. The overheads obtained from this column, which is operated under a pressure of from 20 to 200 mbar and a temperature of from 50° to 65° C., both as measured at the top of the column, and at a reflux ratio of from 0.5 to 8, consist of n-butanol, GBL and the remainder of the ethanol and are fed to the fourth column. The bottoms from the third column comprise a mixture of BD and DES, which is advantageously recycled to the hydrogenation of the diethyl maleate.

In the fourth column, the overheads from the third column are distilled to remove the alcohols ethanol and n-butanol as overheads and the pure GBL through a side outlet. The fourth column has from 10 to 30 theoretical trays. The temperature and pressure at the top of the fourth column range from 45° to 55° C. and from 50 to 500 mbar respectively. The reflux ratio is, for example, from 0.5 to 3. The bottoms obtained in the fourth column comprise a mixture of GBL and high-boiling fractions which have formed during distillation. This mixture may be discharged or, alternatively, recycled to the second column.

The method of the invention makes it possible to isolate GBL from the starting mixture using considerably less apparatus. It is also possible, if necessary, to separate from the GBL, in the fourth column, any low-boiling fractions or high-boiling fractions which may have formed during the various distilling stages. The overheads from the first and fourth columns and the bottoms from the second column may be further purified in conventional manner in order to obtain on-specification THF and BD and an ethanol which can be recycled to the esterification stage.

Since it would have been expected that the presence of ethanol and n-butanol in mixtures containing GBL and DES would have barred all possibility of isolating GBL or DES by distillation, the superior results achieved by the method of the invention must be regarded as being of a surprising nature.

EXAMPLE

A reaction mixture obtained from the catalytic hydrogenation of diethyl maleate was distilled. Its composition was as follows: 48.6% of ethanol, 40.8% of BD, 4.3% of GBL, 4.3% of DES, 1.6% of THF, 0.1% of n-butanol, 0.1% of water and 0.2% of high-boiling fractions.

The distilling plant used is shown diagramatically in the accompanying drawing. 100 parts of the mixture are passed to the first column (1) through the feed line (5). the column has 15 theoretical trays. A temperature of 41° C. and a pressure of 200 mbar, both measured at the top of the column, and a reflux ratio of 0.3 give 500 parts of overheads (6) comprising 96.5% of ethanol, 3.3% of THF and 0.2% of water. The bottoms consist of 500 parts of a mixture comprising 81.6% of BD, 8.6% of DES, 0.6% of ethanol, 0.2% of n-butanol and 0.4% of high-boiling fractions.

100 Parts of bottoms (7) from the first column (1) are passed to the second column (2) having 15 theoretical trays. A temperature of 54° C. and a pressure of 50 mbar, both measured at the top of the column, and a reflux ratio of 1.7 give 18.4 parts of overheads comprising 46.9% of GBL, 46.9% of DES, 0.9% of n-butanol and 2% of BD and 81.6 parts of bottoms comprising 99.6% of BD and 0.4% of high-boiling fractions.

100 Parts of overheads (8) from the second column (2) are passed to the third column (3) having 60 theoretical trays. A temperature of 57° C. and a pressure of 50 mbar, both measured at the top of the column, and a reflux ratio of 1.9 give 51.3 parts of overheads comprising 91.9% of GBL, 1.7% of n-butanol and 6.4% of ethanol and 48.7 parts of bottoms comprising 95.5% of BD and 4.1% of DES.

100 Parts of overheads (9) from the third column (3) are passed to the fourth column (4) having 15 theoretical trays. A temperature of 51° C. and a pressure of 280 mbar, both measured at the top of the column, and a reflux ratio of 0.8 give 8.1 parts of overheads (10) comprising 79.2% of ethanol and 20.8% of n-butanol. 90.6 Parts of GBL having a purity of at least 99.9% are removed through the side outlet (11). The bottoms (12) consisting of 1.3 parts of GBL (99.9% pure) and traces of high-boiling fractions are recycled to the second column (2).

We claim:

1. A method of separating γ-butyrolactone from a mixture containing ethanol, tetrahydrofuran, water, n-butanol, 1,4-butanediol, diethyl succinate and γ-butyrolactone, by distillation, comprising
   (a) separating the THF, water and at least 90% of the ethanol as overheads in a first column having from 5 to 25 theoretical trays and operated at a pressure of from 50 to 500 mbar and a temperature of from 35° to 50° C., both as measured at the top of the column,
   (b) feeding the bottoms from the first column to a second column having from 10 to 30 theoretical trays and operated under a pressure of from 20 to 200 mbar and a temperature of from 45° to 60° C., both as measured at the top of the column, to give overheads consisting of ethanol, n-butanol, γ-butyrolactone, diethyl succinate and 1,4-butanediol,
   (c) feeding the overheads from the second column to a third column having from 40 to 100 theoretical trays and operated under a pressure of from 20 to 200 mbar and a temperature of from 50° to 65° C, both as measured at the top of the column, to give overheads consisting of ethanol, n-butanol and γ-butyrolactone,
   (d) feeding the overheads from the third column to a fourth column having from 10 to 30 theoretical trays and operated under a pressure of from 50 to 500 mbar and a temperature of from 45° to 55° C., both as measured at the top of the column, to give overheads consisting of ethanol and n-butanol, whilst the γ-butyrolactone is removed from the column through a side outlet.

* * * * *